United States Patent [19]
Zeytinoglu et al.

[11] Patent Number: 6,080,539
[45] Date of Patent: *Jun. 27, 2000

[54] IN SITU IMMUNODETECTION OF ANTIGENS

[75] Inventors: Fusun Zeytinoglu, Del Mar; Franz B. Thiebaut, Carlsbad, both of Calif.

[73] Assignee: Greenwich Technologies

[ * ] Notice: This patent issued on a continued prosecution application filed under 37 CFR 1.53(d), and is subject to the twenty year patent term provisions of 35 U.S.C. 154(a)(2).

This patent is subject to a terminal disclaimer.

[21] Appl. No.: 09/168,209

[22] Filed: Oct. 7, 1998

Related U.S. Application Data

[63] Continuation of application No. 08/447,072, May 22, 1995, Pat. No. 5,874,226.

[51] Int. Cl.$^7$ .................................................. C12Q 1/70
[52] U.S. Cl. ................ 435/5; 435/7.1; 435/7.23; 435/7.3; 435/7.31; 435/7.32; 435/7.5; 435/7.72; 435/7.9; 436/64; 436/501; 436/805; 522/98; 424/9.1; 424/9.6; 424/9.8
[58] Field of Search ................ 435/5, 6, 7.1, 7.23, 435/7.3, 7.31, 7.32, 7.5, 7.72, 7.9, 974, 975; 436/501, 64, 805; 422/58; 424/9.1, 9.6, 9.8

*Primary Examiner*—Jeffrey Stucker
*Attorney, Agent, or Firm*—Fish & Associates, LLP; Robert D. Fish

[57] ABSTRACT

An antibody targeted to an antigen is brought into contact with a body component in situ. The resulting antibody/antigen complex is labeled and may be amplified. The label is then detected either in situ or ex situ.

7 Claims, 2 Drawing Sheets

IN SITU IMMUNODETECTION OF ANTIGENS

This application is a continuation of application Ser. No. 08/447,072 filed May 22, 1995, now U.S. Pat. No. 5,874,226.

BACKGROUND

The present invention relates to in situ immunodetection of antigens.

Numerous devices and methods are known for detecting antigens ex situ, i.e., on or within tissue, fluid or other samples that have been removed from the body. In a typical protocol antibodies may be raised against one or more epitopes on a target protein by injecting the protein into a rabbit, human or other host, allowing the host to produce antibodies against the protein, and then removing and purifying sera from the host. The antibody is then brought into contact with the sample under circumstances which are favorable for the formation of an antibody/antigen complex. In cases where the signal is low, such as where the amount of antigen is low or the antigen/antibody binding is poor, one or more amplification steps may be used. Typically, a visible chromophore, radioactive, fluorescent, oligonucleotide or other marker is attached to the antibody or to one of the amplification reagents to facilitate detection of the antigen complex. The terms "label" and "marker" are used herein interchangeably.

Antibodies used in such methods may be more or less specifically selective for the target antigen, and may bind with a greater or lesser efficiency to the target antigen. Typically, useful antibodies will have a good specificity for the target antigen and an association constant (ka) of approximately $10^3$–$10^9$ with the target antigen. Antibodies may also be polyclonal or monoclonal, or some combination of the two.

A known method of immunodetection designed by Charles Cantor uses two different antibodies. A first step biotinylated, monoclonal or polyclonal antibody is used to detect the target antigen(s), and a second step antibody is then used to detect the biotin attached to the complexed biotin. In that method the sample to be tested is first incubated in a solution containing the first step antibody. If the target antigen is present, some of the antibody binds to the antigen to form a biotinylated antibody/antigen complex. The antibody/antigen complex is then amplified by incubation in successive solutions of streptavidin (or avidin), biotinylated DNA, and/or complementary biotinylated DNA, with each step adding additional biotin sites to the antibody/antigen complex. The amplification steps are repeated until a suitable level of amplification is achieved, at which point the sample is incubated in a solution containing the second step antibody against biotin. This second step antibody is labeled, as for example with an enzyme that can be used to detect the presence of the antibody/antigen complex by histoenzymology using a chromogen substrate. With suitable amplification, a conjugate can be produced which is macroscopically visible.

Another known method of immunodetection takes advantage of the immuno-PCR (Polymerase Chain Reaction) methodology (2). The PCR method is similar to the Cantor method up to the incubation with biotinylated DNA, however, instead of using multiple rounds of streptavidin and biotinylated DNA incubation, the DNA/biotin/streptavidin/antibody complex is washed out with a low pH or high salt buffer that releases the antibody. The resulting wash solution is then used to carry out a PCR reaction with suitable primers with appropriate controls. At least in theory, the enormous amplification capability and specificity of PCR can be utilized to detect a single antigen molecule.

Still other methods may utilize synthetic antibodies such as those available through molecular imprinting technology (see, e.g., U.S. Pat. No. 5,110,833 to Mosbach). As used herein, the terms "antibody" and "antibodies" include synthetic antibodies and other antibody analogs.

While these and other known methods of immunodetection have been applied to nonliving materials, and to living cells ex situ (e.g., tumor cells (3), they have never to our knowledge been applied in situ. As used herein in situ refers to tissues, cells, fluids and other body components that are still coupled to the body during the antibody binding step, as opposed to having been biopsied or otherwise removed from the body for the antigen binding step.

Application of antigen detecting methods to in situ body components is highly desirable. For example, such methods can be performed outside the confines of a laboratory or clinical setting, without the taking of tissue samples. Where the results are visualized macroscopically, the methods can also be performed without the need for specialized equipment such as microscopes or plate readers (4). In situ detection of antigens on a body surface such as the skin of a patient, for example, can facilitate field screening of numerous pathogenic agents such as virus, bacteria, fungi and mycoplasma appearing on the skin surface, and assist in the diagnosis of skin conditions such as psoriasis. In situ detection of antigens may also be used to detect antigens which are present below the surface of the skin, such as where the detection takes place in an open wound or an incision, or in a body cavity. In these and other instances, antigens are said to be proximally associated with a body component if they can be detected with application of one or more of the devices and methods disclosed herein to the body component.

Due to the presence of Langerhans and other specialized cells in the skin, in situ immunodetection of antigens may also be useful in the diagnosis and prognostication of systemic diseases including AIDS and some cancers. Langerhans are professional antigen presenting cells (APCs) which comprise approximately 2% of the human skin cell population. They function both as the skin's antigen presenting cells and as depositories for foreign antigenic fragments, accumulating and presenting at the skin surface circulating antigens characteristic of a broad range of localized and systemic conditions. In the case of AIDS, for example, it is known that human immunodeficiency virus can infect Langerhans cells, (5), and that resident Langerhans cells can contain the HIV-1 gag protein and have viral particles budding from their membranes (6,7). Proviral DNA (5) and tat, rev, nef and env mRNA (8) have been demonstrated in Langerhans cells, and HIV-specific nucleic acids have been detected on the surface of biopsied skin specimens using PCR (8).

Of course, in situ immunodetection of disease conditions need not necessarily rely on Langerhans cells. Keratinocytes, for example, are epidermal cells which are primary targets of Human Papilloma Virus (HPV), and a topical test for HPV antigens could be developed in accordance with the devices and methods disclosed herein.

Thus, there is a need to provide devices and methods for in situ immunodetection of antigens.

SUMMARY OF THE INVENTION

The present invention involves immunodetection of antigens in which an antibody is brought into contact with a body component in situ, and the resulting antibody/antigen complex is then detected either in situ or ex situ.

In one aspect of the invention, a retainer is applied to a body part such as the skin or mucous membrane of a patient, and one or more first step antibodies are brought into contact with the body part within the confines of the retainer. Some of the first step antibody binds to antigens present at or near the body part, and unbound first step antibody is washed away. Antibody/antigen complex may then be amplified to an appropriate level, and a second step antibody is brought into contact with the antibody/antigen complex to render the complex macroscopically detectable.

In another aspect of the invention, the bound antibody is removed from the body part and processed ex situ. For example, the bound antibody/antigen complex can be washed out, and the resulting wash solution can be used to carry out a PCR reaction.

Other aspects of the invention involve modifications to the retainer(s). For example, a first retainer may comprise a bandage which holds an antibody impregnated paste in contact with a skin surface. After an appropriate incubation period, the bandage is removed and the bound antibody/antigen complex is processed in situ, ex situ, or using some combination of the two.

Still other aspects of the invention include panels or series of tests for screening purposes.

BRIEF DESCRIPTION OF THE DRAWING

These and other aspects of the present invention will become better understood through a consideration of the following description taken in conjunction with the drawing in which like numerals represent like components.

BRIEF DESCRIPTION OF THE DRAWING

Figure 1:
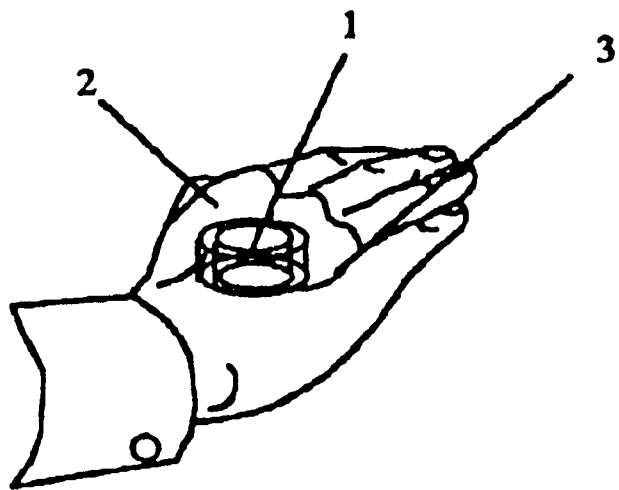
FIG. 1 is a diagrammatic representation of the application of a ring-shaped retainer to the skin of a patient.

In FIG. 1, a retainer 1 is applied to the skin on the back of a patient's hand 2. In this instance the retainer 1 is a ring approximately 1 cm in diameter and 0.5 cm. high, and the retainer 1 is manufactured from polypropylene plastic. Of course, other sizes and shapes and other materials which minimize interference with the procedures may also be used. An adhesive layer 3 preferably coats the base of retainer 1, and serves to adhere and conform the retainer 1 to the hand 2. In a preferred embodiment, the adhesive comprises removable double-sided mounting squares such as 3M Scotch™ squares available from Boise Cascade office products, tel: 800-562-1746.

Numerous alternatives to the retainer 1 shown in FIG. 1 are possible. Alternative retainers may, for example, have some other cross-sectional shape such as oval or polygonal. They may also have dividers separating the testing area into multiple compartments or wells. Also, retainers need not have adhesive on the bottom surface, but may be affixed, i.e., kept in juxtaposed relation with the skin or other body component, by other means such as an elastic band or a bandage. Alternative retainers may also be constructed of a flexible material such as an adhesive bandage, having, for example, a patch of cloth impregnated with antibodies. Where the body component being tested is below the normal surface of the skin, such as may be present with a wound, blister or chancre, or when the body component being tested is a mucous membrane, the retainer may be affixed to the skin adjacent to the testing area.

It is also possible to provide a retainer having a cavity adapted to receive a body component, rather than adapted to be affixed to a body component. For example, a retainer may comprise a test tube or beaker containing one of the reagents, and a body component such as a finger can be brought into contact with the reagent by inserting the body component into the retainer.

Still other embodiments are possible, provided that some means is used to maintain contact between certain reagents and the body component being tested for suitable periods of time. These periods of time may have larger or smaller acceptable ranges, depending on many factors including surface and ambient temperature, and the reagent being utilized. Thus, it may be possible to perform the necessary steps without any retainer at all, as for example where the body component being tested comprises a wound or invagination, or presents a cupped surface such as a hand. It may also be possible to perform the necessary steps without any retainer for steps in which the reagent is sufficiently viscous to maintain its contact with the body component.

Figure 2:
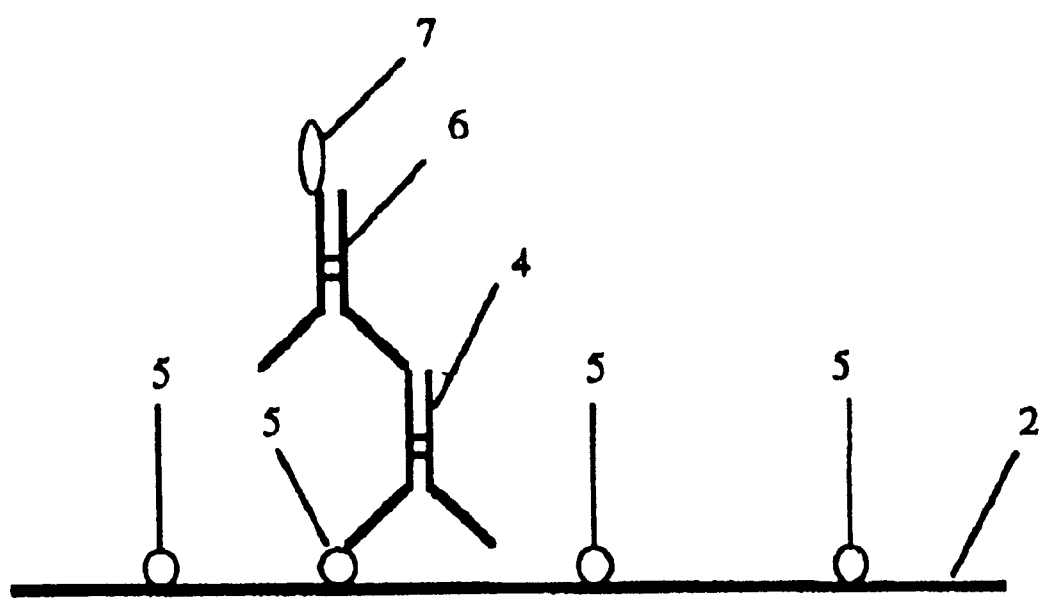
FIG. 2 is a diagrammatic representation of a process for detecting antigen on a body part using first and second step antibodies.

In FIG. 2, a first step antibody 4 is brought into contact with the skin or other body component 2 in situ, where it has an opportunity to contact the targeted antigen(s) 5. The first step antibody 4 must be able to bind with at least one antigenic determinant on the targeted antigen, and is preferably of the monoclonal or polyclonal type due to the availability of raising antibodies in those forms to essentially any identifiable antigen. First step antibodies can be produced according to one of the classical method of antibody production. (11) Such antibodies may be more or less selective to the target antigen, and may bind more or less strongly to the target antigen. In some instances the use of polyclonal antibodies will be advantageous because they have the ability to recognize multiple epitopes, however, the use of polyclonal antibodies generally also results in reduced specificity. Where monoclonal first step antibodies are used, it is preferable to raise the antibodies against an epitope in it natural conformation (9) to aid in binding. Some combination of monoclonal or polyclonal antibodies may also be used, such as in a screening panel.

In a preferred embodiment the first step antibody 4 is conjugated to biotin (biotinylated). Other labels may be used, including peroxidase and alkaline phosphatase, and it is also possible to utilize the first step antibody 4 without being conjugated to any label at all. The first step antibody 4 may be present in many forms, including a liquid solution or a viscous paste. The first step antibody 4 may also be deposited on a surface, such as an adhesive bandage, which is brought into contact with the body component 2 being investigated.

Also shown in FIG. 2 is a second step antibody 6 selectively binding to the first antibody 4. The second step antibody 6 is advantageously of the polyclonal antibody type because of its ready availability, lower cost and its ability to give a stronger signal, and is preferably included in a liquid solution for ease of use. The second step antibody 6 may be conjugated to biotin markers 7, or it may alternatively be bound to colloidal gold, an enzymatic fragment, or any other appropriate colored or chromogen substance including chromophore, dye, or liposome loaded with dye.

Implicit in FIG. 2 is the use of necessary reagents to carry out the testing. Where the testing is performed on living tissue, it is obviously desirable to use nontoxic and nonirritating reagents, but these are not absolute requirements, and any negative effects must be weighed against the value of the testing.

An amplification step may or may not be employed, depending on the strength of the signal and the signal to noise ratio. This in turn depends on many factors known to those in the art, including as the amount of antigen and the strength of the antigen/antibody binding. Where an amplification step is utilized, the amplification step preferably comprises the biotin, streptavidin, a biotinylated DNA technology described by Cantor (1), which article is incorporated herein in its entirety. Other amplification technologies are also applicable, including two steps, 3 steps, PAP, and APAAP methods.

In one possible amplification step, (not shown), a fragment of nucleic acid or an analog such as a molecular polymer can be used to bind to the streptavidin/biotin/ antibodies complex. If such a fragment is used, it should be rare enough to diminish the possibility of amplifying an unrelated DNA fragment. A gene fragment from a thermophile bacterium, for example, is a good candidate (10). Such a fragment can also be labeled with a biotin or other marker such as a fluorescent dye, although labeling with a staining substance is preferred so that the streptavidin/biotin/ antibodies complex can be conveniently detected with the unaided eye.

Figure 3:
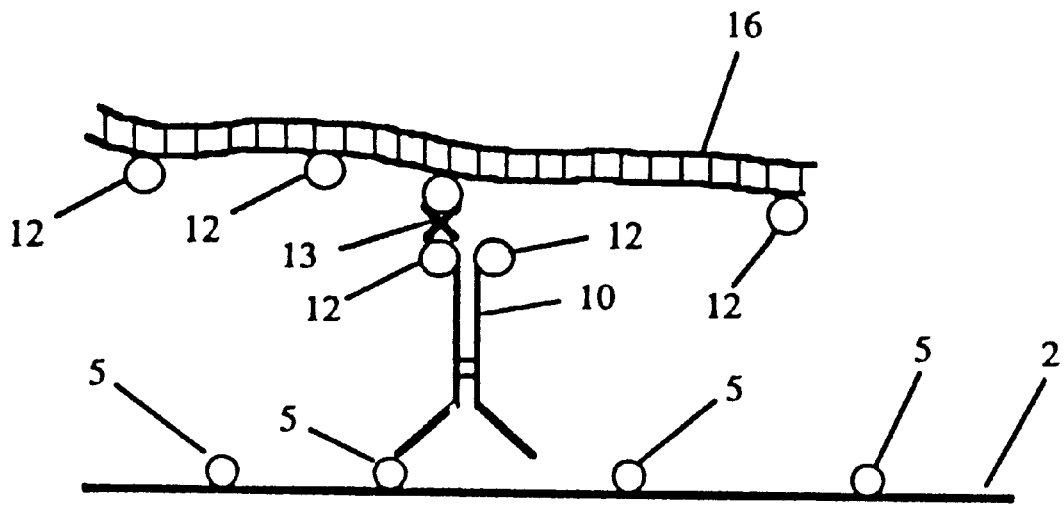
FIG. 3 is a diagrammatic representation of a process for detecting antigen on a body part using Immuno-PCR.

In FIG. 3, antibody 10 binds selectively to target antigen (s) 5, and the resulting antibody/antigen complex is washed out with a low pH buffer that releases the antibody. Numerous means can be used to achieve adequate antibody elution. For example, in cases where the background signal is too high, a high pH buffer of Sodium Citrate pH 6.0 0.1M can be used to wash the sample before elution. For antibody/ streptavidin/biotin/DNA complex elution, one can use (1) a high salt concentration (1–2M) of NaCl in PBS buffer pH 7.1, (2) a low pH (3.5) sodium citrate buffer 0.1M, (3) WALPOLE (acetic Acid Sodium Acetate) buffer at pH 3.5, or (4) a solution of 0.5–2% sodium dodecyl sulfate. The resulting wash solution is used to carry out a PCR reaction, which serves to amplify the bound DNA. While other amplification steps can be used, FIG. 3 depicts the use of biotinylated 12 first step antibody 10, biotinylated 12 streptavidin 14, and PCR operating on biotinylated DNA 16 according the disclosure of (2), which is incorporated herein in its entirety. The PCR amplification method shown is especially advantageous where the amount of antigen to be detected is very small, e.g., 500 molecules.

Figure 4:
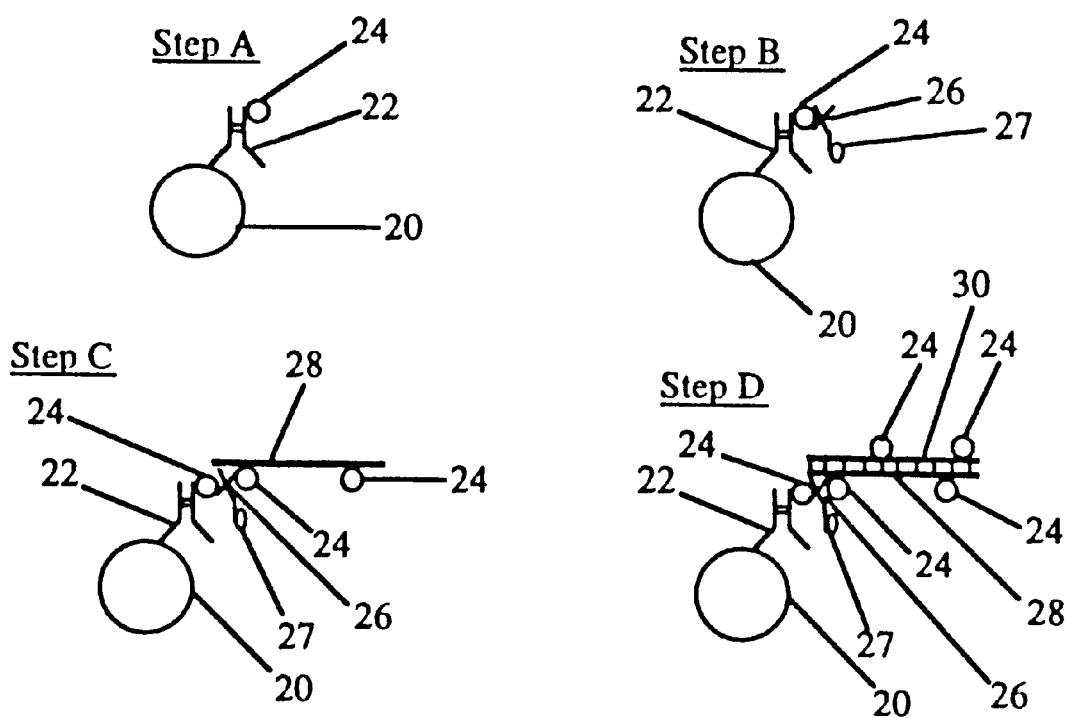
FIG. 4 depicts significant sequential steps from an alternative protocol for identifying antigen.

FIG. 4 depicts steps from an alternative protocol for identifying antigen. In step A, a biotinylated 24, monoclonal antibody 22 is allowed to bind to cell surface antigen 20. In step B, streptavidin 26 having a marker such as colloidal gold 27 is then bound to the biotin molecule 24 of the antibody 22. In step C, biotinylated single strand DNA (ssDNA) 28 is bound to the streptavidin 26, and in step D, complementary biotinylated 24 DNA 30 hybridizes to the already complexed DNA 28.

USE OF THE INVENTION

The devices and methods disclosed herein can be used to identify a broad range of pathogenic agents including virus, bacteria, fungi, mycoplasma, along with the detection and diagnosis of systemic diseases including but not restricted to AIDS, HIV, hepatitis A, B, C and tuberculosis. The devices and methods disclosed herein may also be used as a screening tool, and for prognostication and follow up of a treatment regimen. For example, the human papilloma virus (HPV) family consists of closely related strains, and in order to develop an effective therapeutic strategy against a specific strain, an accurate identification tool is required. A topical skin test such as the one described above constitutes such a tool. Another exemplary usage involves the differential diagnosis between melanoma and fungal skin infection. The current procedure usually requires a biopsy and subsequent examination of the sample by a pathologist. Such a procedure is not only expensive and time consuming, but it is also invasive. By comparison, a surface skin test under the procedure of example 2 below can be used to make the differential diagnosis, but has tremendous advantages in time, cost reduction and non-invasiveness.

The devices and methods disclosed herein may also have significant advantages in terms of the flexibility of the mode of delivery. For example, some tests in accordance with the disclosure herein can be used without a laboratory, and can be both non-invasive and nontoxic. Such tests can be utilized advantageously not only by clinicians, hospitals, reference laboratories, and public health facilities, but also by field workers in under and undeveloped areas throughout the world.

EXAMPLE 1

A test involving a Cantor-type amplification can be performed as follows:

SOLUTION A: General Buffer

D-PBS pH 7.1 (Dulbecco formula) with Calcium & Magnesium (ICN Cat No:18-610-54)

$CaCl_2$ anhyd. 0.10 g/L

Kcl 0.20 g/L $KH_2PO_4$ 0.20 g/L $MgCl_2$ $6H_2O$ 0.10 g/L

NaCl 0.80 g/L $NaH_2PO_4$ $7H_2O$ 2.16 g/L

SOLUTION B: Blocking Buffer 2 mg/ml bovine serum albumin (crystalline) (ICN Cat No:103700) in D-PBS pH 7.1 (Dulbecco formula) with Calcium & Magnesium (ICN Cat No:18-610-54).

SOLUTION Ca: First Step Antibody 1 z1 ml of 1/1000 dilution in solution B of concentrated serum candida albicans goat polyclonal (Immunomycologics Inc., tel: 800-654-3639.)

SOLUTION Cb: First Step Antibody 2

1 ml of 10 ug/ml of mab NKI-C3 anti Melanoma associated Ag 25/100 kd IgG1MAB (Caltag Laboratory, Inc., tel: 800-874-4007) in solution B.

SOLUTION Da: Second Step Antibody 1

50 ug/ml of biotinylated Donkey anti Goat IgG(H+L) in solution B. (Jackson Immunoresearch cat no.: 705-065-003, tel: 800-367-5296).

SOLUTION Db: Second Step Antibody 2

50 ug/ml of biotinylated Goat antimouse IgG(H+L) in solution B. (Jackson Immunoresearch, cat: 115-035-003, tel:800-367-5296).

SOLUTION E: Streptavidin/20 nm Gold Solution 10 ug/ml streptavidin 20 nm gold (ICN cat No 67-870-2, tel:800-854-0530).

SOLUTION F: Biotinylated DNA Solution 100 ug/ml in solution B. The DNA has the following sequence, which is the first 300 nucleotides of the DNA repair gene recA of *Thermus aquaticus* bacteria (10).

```
5' GAGCCAGGCC CTGAGGAAGC TGACCGCCGT CCTCTCCAAG AGCAACACCG
   CCGCCATCTT CATCAACCAG GTGCGGGAGA AGGTGGGGGT CATGTACGGC
   AACCCCGAGA CCACGCCGGG CGGCCGGGCC CTCAAGTTCT ACTCCAGCGT
   GCGCCTGGAC GTGCGCAAAA GCGGCCAGCC CATCAAGGTG GGCAACGAGG
   CCGTGGGCAT CAAGGTCAAG GTCAAGGTGG TGAAGAACAA GCTGGCCCCG
   CCCTTCCGGG AGGCGGAGCT 3'
```

The DNA is labeled with biotin-14-dCTP using the random priming method (i.e., Bioprime non radioactive DNA labeling system Cat No: 18094-011 Gibco BRL, Tel: 800-828-6686) or other alternative methods (i.e., PCR).

In the Clinical Facility:

1) Prepare the skin by rubbing it with 70% ethanol, peel off the adhesive ring protection and attach the ring to the skin.
2) Rinse inside the ring with 1 ml solution A.
3) Add 0.5 ml of solution C (first step antibody), waits 3 min.
4) Rinse 3 times with solution A.
5) Add 0.5 ml of solution D (second step antibody) and wait 3 min.
6) Rinse 3 times with solution A.
7) Add 0.5 ml of solution E (streptavidin/gold solution) and wait 3 min.
8) Rinse 3 times with solution A.
9) Add 0.5 ml of solution F (biotin/DNA) and wait 5 min.
10) Rinse 3 times with solution A.
11) Add 0.5 ml of solution E (streptavidin/gold solution) and wait 3 min.

The appearance of a red immunostain indicates a positive result.

EXAMPLE 2

A test involving PCR amplification can be accomplished in the following manner. The following reagents are prepared and/or acquired:

SOLUTION A: General Buffer

D-PBS pH 7.1 (Dulbecco formula) with Calcium & Magnesium, ICN Cat No:18-610-54

CaCl2 anhyd. 0.10 g/L
Kcl 0.20 g/L
KH2PO4 0.20 g/L
MgCl2 6H2O 0.10 g/L
NaCl 0.80 g/L
NaH2PO4 7H2O 2.16 g/L SOLUTION B: Blocking Buffer 2 mg/ml bovine serum albumin (crystalline) (ICN Cat No:103700) in D-PBS pH 7.1 (Dulbecco formula) with Calcium & Magnesium (ICN Cat No:18-610-54).

SOLUTION Ca: First Step Antibody 1

1 ml of 1/1000 dilution in solution B of concentrated serum *Candida albicans* goat polyclonal Ab (Immuno-Mycologics Inc., tel: 800-654-3639).

SOLUTION Cb: First Step Antibody 2

1 ml of 10 ug/ml of mab NKI-C3 anti-Melanoma associated Ag 25/110 kd IgG1MAB (Caltag Laboratory Inc., tel: 800-874-4007) in solution B.

SOLUTION Da: Second Step Antibody 1

50 ug/ml of biotinylated Donkey anti-Goat IgG(H+L) from (Jackson Immunoresearch, Cat: 705-065-003, tel: 800-367-5296) in solution B.

SOLUTION Db: Second Step Antibody 2

50 ug/ml of biotinylated goat antimouse IgG(H+L) from (Jackson Immunoresearch, Cat: 115-065-003, tel: 800-367-5296) in solution B.

SOLUTION E: Streptavidin Solution 10 ug/ml streptavidin from (Jackson Immunoresearch, Cat: 016-000-084, tel: 800-367-5296).

SOLUTION F: Biotinylated DNA Solution 100 ug/ml in solution B. The DNA has the following sequence, which is the first 300 nucleotides of the DNA repair gene recA of *Thermus aquaticus* bacteria (10).

```
5' GAGCCAGGCC CTGAGGAAGC TGACCGCCGT CCTCTCCAAG AGCAACACCG
   CCGCCATCTT CATCAACCAG GTGCGGGAGA AGGTGGGGGT CATGTACGGC
   AACCCCGAGA CCACGCCGGG CGGCCGGGCC CTCAAGTTCT ACTCCAGCGT
   GCGCCTGGAC GTGCGCAAAA GCGGCCAGCC CATCAAGGTG GGCAACGAGG
   CCGTGGGCAT CAAGGTCAAG GTCAAGGTGG TGAAGAACAA GCTGGCCCCG
   CCCTTCCGGG AGGCGGAGCT 3'
```

The DNA is labeled with the biotin-14-dCTP using the random priming method (i.e.: Bioprime non radioactive DNA labeling system (Gibco BRL, Cat No: 18094-011, tel: 800-828-6686), or other alternative methods that can be used to incorporate biotinylated nucleotides in a 300 bp DNA sequence.

SOLUTION G: Eluting Solution (1M NaCl/PBS)

NaCl: 58.44 g/L in solution A.

In The Clinical Or Testing Facility:

(1) Prepare the skin of the patient in situ by rubbing it with 70% ethanol.
(2) Peel off the adhesive protection of the work space ring or other retainer as described above, and affix the retainer to the skin to define the area of skin to be tested (the testing area).

(3) Rinse the testing area and the entire work space with 1 ml of solution A.

(4) Add 0.5 ml of solution C (first step antibody) to the testing area, and wait 3 min.

(5) Rinse the testing area and the entire work space 3 times with solution A.

(6) Add 0.5 ml of solution D (second step antibody) to the testing area and wait 3 min.

(7) Rinse the testing area and the entire work space 3 times with solution A.

(8) Add 0.5 ml of solution E (streptavidin solution) to the testing area and wait 3 min.

(9) Rinse the testing area and the entire work 3 times with solution A.

(10) Add 0.5 ml of solution F (biotin/DNA) to the testing area and wait 5 min.

(11) Rinse the testing area and the entire work 3 times with solution A.

(12) Add 0.3 ml of solution G (1 m NaCl/PBS) to the testing area and wait 2 min.

(13) Recover the used solution G into a sterile tube as the sample, and add 0.7 ml absolute ethanol. Ship the sample to the laboratory.

In The Laboratory:

(14) Store the sample at −20C over night because it helps precipitate the DNA.

(15) Spin down the tube containing the sample at 14K G for 15 min at 4C.

(16) Re-suspend the sample in 10 ul Tris EDTA buffer (TE).

(17) Use the DNA to carry out a PCR amplification of the recA gene fragment with the following primers:

```
P1: 5' TCC TCT CCA AGA GCA ACA CC 3'
P2: 5' CCA GCT TGT TCT TCA CCA CC 3'
```

(18) The presence of a PCR product indicates a positive result. The absence of a PCR product indicates a negative result.

EXAMPLE 3

A diagnostic kit for performing immunodetection in situ on skin comprises the following items:

(1) A solvent such as ethanol, acetone or saponin which increases the accessibility of the immunoassay target molecules in skin cells.

(2) An adhesive ring which can be removably adhered to a skin surface. The ring forms a well within which various reagents solutions are applied.

(3) A first step antibody solution.

(4) A second step antibody solution. This antibody binds to the first step antibody, and is conjugated to either colloidal gold or to some other contrasting dyes and/or enzymatic markers.

(5) One or more of the following: (a) a chromogen reagent such as 3-amino-9-ethyl carbazole (AEC); (b) a solution of streptavidin; ⓒ Biotinylated DNA.

(6) A non toxic washing buffer such a phosphate buffer saline or WALPOLE (Acetic Acid/Sodium acetate).

The immunodetection procedure consists generally of two short incubations with the antibody solutions, and two washes with a non-toxic phosphate buffer saline (PBS) solution. Performing these applications takes approximately fifteen to thirty minutes and requires no special skills.

The kit is utilized as follows:

(7) An area of the patient's skin cleaned with ethanol, and the adhesive ring is removably adhered to the cleaned area. In its adhered position the ring defines the area of skin to be tested (the testing area).

(8) The first step antibody solution is brought into contact with the testing area.

(9) After 5 minutes of incubation, the testing area and the entire work space is washed briefly with a phosphate buffer solution at pH 7.1 to remove non-bound antibody.

(10) The second step antibody solution is brought into contact with the testing area.

(11) The testing area is washed with a phosphate buffer solution at pH 7.1

(12) If an enzyme is used as a label, an appropriate chromogen reagent such as 3-amino-9-ethyl carbazole (AEC) is brought into contact with the testing area.

6a) If biotin is used as a label, a solution of streptavidin is brought into contact with the testing area. The streptavidin is incubated for 5 minutes, and then the testing area and the entire work space is washed with a solution of phosphate buffer.

6b) Biotinylated DNA is brought into contact with the testing area. After 10 minutes the testing area and the entire work space is washed with phosphate buffer at pH 7.1, and then incubated with WALPOLE (acetic Acid Sodium Acetate) buffer at pH 3.5 for 5 minutes.

6c) The WALPOLE buffer is neutralized with 10X phosphate buffer and recovered.

6d) A portion of the WALPOLE/phosphate buffer is then used for polymerase chain reaction using the appropriate primers. Primers to amplify the DNA fragment probe are known to those in the art. The polymerase chain reaction can be performed using a commercially available thermocycler, and the presence or absence of a product can be tested by gel electrophoresis.

EXAMPLE 4

*Candida albicans* can be detected using the devices and methods disclosed above in conjunction with one or more of the following reagents available from the source indicated:

a. goat polyclonal Ab, Memorial Sloan-Kettering Cancer Inst.
b. rabbit polyclonal Ab, Biodesign International
c. goat polyclonal Ab,Immuno-mycologics Inc.
d. mouse mab, Virostat
e. mouse mab, Chemicon International
f. mouse mab, Biodesign International

EXAMPLE 5

Aspergillus can be detected using the devices and methods disclosed above in conjunction with one or more of the following reagents available from the source indicated:

Aspergillus c.
a. fixing goat polyclonal Ab, Immuno-mycologics, Inc.
b. gel diffusion goat polyclonal Ab, Immuno-mycologics, Inc.

*Aspergillus mycelia*
c. goat polyclonal Ab, Meridian Diagnostic Inc.

EXAMPLE 6

*Clostridium perfringens,* bacteria associated with gangrene, can be detected using the devices and methods disclosed above in conjunction with one or more of the following reagents available from the source indicated:

*Clostridium perfringens* ABCD
a. ABCD rabbit polyclonal Ab, Accurate Chem. & Scientific Co.
*Clostridium perfringens* C
b. goat polyclonal serum, Techlab
*Clostridium perfringens* D
C. goat polyclonal serum, Techlab
*Clostridium perfringens* E
d. goat polyclonal serum, Techlab

EXAMPLE 7

Bacteria and toxoid associated with tetanus can be detected using the devices and methods disclosed above in conjunction with one or more of the following reagents available from the source indicated:

*Clostridium tetani*
a. human Ig polyclonal Ab, Massachusetts Biological lab or MILES INC.
*Clostridium tetani* toxoid
b. human serum polyclonal Ab, North American Biological Inc.

EXAMPLE 8

Herpes viruses can be detected using the devices and methods disclosed above in conjunction with one or more of the following reagents available from the source indicated:

Herpes simplex type 1
a. Goat serum, Biochemed Corp. CA
b. goat polyclonal IgG, Biodesign International
c. Mouse mab, Biogenesis.
Herpes simplex type 2
d. rabbit polyclonal Ab, Cortex Became.
e. rabbit serum polyclonal IgG, Biogenesis LTD.
f. mouse mab, Cortex Became
g. mouse mab, Media Batik, Inc.

EXAMPLE 9

Papilloma virus can be detected using the devices and methods disclosed above in conjunction with one or more of the following reagents available from the source indicated:

Papilloma Virus in general
a. mouse mab, Passel & Lore GmbH & Co.
b. rabbit polyclonal Ab, Zymed laboratory
Papilloma Virus type 1,6,11,16,18,31
c. IgG mouse mab, Chemicon International Inc.
Papilloma Virus type 16,E1,E4
d. IgG1 17D5 mab purified, Pharmigen

EXAMPLE 10

*Mycobacterium leprae,* the bacteria associated with leprosy (Hansen's disease) can be detected using the devices and methods disclosed above in conjunction with one or more of the following reagents available from the source indicated:
a. cell wall protein IgG1 mab, NIAID Leprosy Program
b. major membrane protein IgG1 mab, NIAID Leprosy Program
c. bacterioferitin IgG1 mab, NIAID Leprosy Program
d. cell wall protein poly-clonal Ab, NIAID Leprosy Program
e. cell wall protein poly-clonal Ab, NIAID Leprosy Program f. phenolic glycolipid poly-clonal Ab, NIAID Leprosy Program

EXAMPLE 11

*Treponema pallidum,* the bacteria associated with syphilis, can be detected using the devices and methods disclosed above in conjunction with one or more of the following reagents available from the source indicated:
a. human serum, polyclonal WHO-3, International Lab For Biol.
b. rabbit serum Ig, polyclonal, Becton Dickinson Microbiology
c. vdr1-reactive human serum, polyclonal, Biomedical Resources
d. RPR-reactive human serum 2173, Scimedx Corp.

EXAMPLE 12

Melanoma associated antigens can be detected using the devices and methods disclosed above in conjunction with one or more of the following reagents available from the source indicated:
a. 25/110 kd IgG1 mab NKI-C3, CALTAG LABORATORY INC.
b. IgG1 95/100 kd IgG1 mab, PAL-M2 ACC, Accurate Chemical & Sci. Co.
c. IgG1 PAL-M1 mab, Accurate Chemical & Sci. Co.
d. Other—The Linscott's directory contains more than 30 entries for anti-melanoma antibodies. ('94–'95 Ed., 4877 granges road Santa Rosa, Calif., 95404 USA, Tel:(707) 544-9555 Fax:(415) 389-6025)

EXAMPLE 13

HIV virus associated with AIDS can be detected using the devices and methods disclosed above in conjunction with one or more of the following reagents available from the source indicated:
a. HIV gp41 antibody MAb 2A2, ICN Pharm. cat: 158366, 1995
b. HIV gp120, antibody MAb 1c1, ICN Pharm. cat: 158367, 1995
c. HIV VAR2, Advanced Immunochemical Inc.
d. HIV P17, Cellular Product Inc.
e. HIV1 ENV HL1, Biodesign International
f. Other—The Linscott's directory contains more than 70 entries for both monoclonal and polyclonal anti-HIV antibodies

EXAMPLE 14

Leukemias can be detected using the devices and methods disclosed above in conjunction with one or more of the following reagents available from the source indicated:

Leukemia HTLV
a. HTLV P19 IgG2a mouse mab, Dupont-Nemours Research products
b. HTLV-I IgG1 mouse mab, 0.5 α NIH-11, Nat'l Institutes of Health, Rockville, Md.
c. HTLV-gp21 IgG1, Chemicon International Inc.
d. HTLV-I&II p24 IgG1 6f10 mouse mab, Sera-Lab Ltd.
e. HTLV-I GAG P19 111–130, frag sheep purified polyclonal, AALTO Bio Reagents Ltd., Publim 14, Ireland
f. HTLV-I p19/28 mouse mab, Chemicon International Inc.
g. Other—The Linscott's directory contains more than 25 entries for both Leukemia HTLV antibodies

EXAMPLE 15

Many other systemic diseases can be detected using the devices and methods disclosed above in conjunction with one or more available antibodies. Such diseases include polyoma, measles and rubella, for which antibodies are listed in the Linscott's Directory.

REFERENCES

1) Cantor C. R. Nucleic Acid binding drug symposium Palo Alto Calif. Jan. 30 1994

2) Sano T., Smith C L., Cantor C R., Immuno-PCR: very sensitive antigen detection by means of specific antibody-DNA conjugates. Science 1992 258: 120–122.

3) Gottesman, M. M., Willingham, M. C., Thiebaut, F., Pastan, I. Expression of the MDR1 gene in normal human tissues. Molecular and Cellular Biology of Multidrug Resistance in Tumor Cells, (Roninson, I., ed.) Plenum Publishing Corp., New York, N.Y., 1989.

3) Levy J A. Pathogenesis of human immunodeficiency virus infection. Microbiol. Rev. 57:183–289 1993 20).

4) Gown A M., In: DeLellis R A (ed) Advances in Immunohisto-chemistry. New York: Raven Press 31–45 1988

5) Zanbruno G., Mori L., Marconi A., Mongiardo N., de Rienzo B., Bertazzoni U., Giannetti A. Detection of HIV-1 in epidermal Langerhans cells of HIV—infected patient using the polymerase chain reaction. J. Invest. Dermatol. 96:979–982 1991

6) Tschachler E., Groh V., Popovic M., Mann D., Konrad K., Safai B., Eron L., Dimarzo Veronese F., Wolff K., Stingl G.

Epidermal Langerhans cells a target for HTLV-III/LAV infection. J. Invest. Dermatol. 88:233–237 1987.

7) Rappersberger K., Gartner S., Schenk P., Stingl G., Groh V., Tschachler E., Mann D., Wolff K., Konrad K., Popovic M. Langerhans Cells are an actual site of HIV-1 replication. Intervirology 29:185–194 1988

8) Kanitakis J., Escaich S., Trepo C., Thivolet J. Detection of human immunodeficiency virus-DNA and RNA in the skin of HIV-1 infected patients using the polymerase chain reaction. J. Invest. Dermatol. 97:91–96 1991

9) Gottesman, M. M., Golstein, L. J., Bruggemann, E., Currier, S. J., Galski, H., Cardarelli, C., Thiebaut, F., Willingham, M. C., Pastan, I. 1988 Molecular diagnosis of multidrug resistance. In Molecular Diagnosis of Cancer, Cold Spring Harbor Laboratory, Cold Spring Harbor, N.Y., 7:75–80, 1989.

10) Angov, E. and Camerini-Otero, R. D. The recA gene from the thermophile *Thermus aquaticus* YT1: cloning, expression, and characterization. J. Bacteriol. 176, 1405–1412 (1994)

11) Current protocols in immunology National Institutes of Health Greene Wiley Editor Collican J. E. et Al. 1991.

---

---

What is claimed is:

1. A method of screening a skin for a skin pathogen comprising:

providing a retainer with a plurality of compartments, wherein a first compartment comprises a first antibody and a second compartment comprises a second antibody;

wherein the first antibody is specifically selective to a first skin pathogen and the second antibody is specifically selective to a second skin pathogen;

contacting a portion of the skin in situ with the retainer;

allowing at least one of the first and second antibodies to bind with the skin pathogen to form at least one an antibody/antigen complex;

labeling the antibody/antigen complex; and identifying the skin pathogen by detecting the label.

2. The method of claim 1 wherein the skin pathogen comprises a virus.

3. The method of claim 2 wherein the virus is a papilloma virus.

4. The method of claim 1 wherein the pathogen comprises a fungus.

5. The method of claim 4 wherein the fungus is *Candida albicans*.

6. The method of claim 1 wherein the pathogen comprises a bacterium.

7. The method of claim 6 wherein the bacterium is *Mycobacterium leprae*.

* * * * *

SEQUENCE LISTING

<160> NUMBER OF SEQ ID NOS: 1

<210> SEQ ID NO 1
<211> LENGTH: 270
<212> TYPE: DNA
<213> ORGANISM: Thermus aquaticus

<400> SEQUENCE: 1

```
gagccaggcc ctgaggaagc tgaccgccgt cctctccaag agcaacaccg ccgccatctt      60
catcaaccag gtgcgggaga aggtgggggt catgtacggc aacccgaga  ccacgccggg     120 cggccgggcc ctcaagttct actccagcgt gcgcctggac gtgcgcaaaa gcggccagcc     180
catcaaggtg ggcaacgagg ccgtgggcat caaggtcaag gtcaaggtgg tgaagaacaa     240
gctggccccg cccttccggg aggcggagct                                       270
```